United States Patent
Reynolds

(10) Patent No.: US 9,675,317 B2
(45) Date of Patent: Jun. 13, 2017

(54) INTERFACE IDENTIFICATION APPARATUS AND METHOD

(71) Applicant: Toshiba Medical Systems Corporation-, Otawara-shi (JP)

(72) Inventor: Steven Alexander Reynolds, Edinburgh (GB)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 118 days.

(21) Appl. No.: 14/578,607

(22) Filed: Dec. 22, 2014

(65) Prior Publication Data

US 2016/0180528 A1  Jun. 23, 2016

(51) Int. Cl.
| | |
|---|---|
| *G06T 1/00* | (2006.01) |
| *A61B 8/08* | (2006.01) |
| *A61B 5/055* | (2006.01) |
| *A61B 6/00* | (2006.01) |
| *G06T 7/11* | (2017.01) |
| *G06T 7/174* | (2017.01) |
| *A61B 6/03* | (2006.01) |

(52) U.S. Cl.
CPC .............. *A61B 8/08* (2013.01); *A61B 5/055* (2013.01); *A61B 6/032* (2013.01); *A61B 6/5217* (2013.01); *G06T 7/11* (2017.01); *G06T 7/174* (2017.01); *A61B 6/037* (2013.01); *A61B 8/0858* (2013.01); *G06T 2207/10072* (2013.01); *G06T 2207/30061* (2013.01)

(58) Field of Classification Search
CPC ... G06T 7/0012; G06T 7/0016; G06T 7/0024; G06T 7/0038; G06T 7/0097; G06T 7/10; G06T 7/13; G06T 7/174; G06T 7/30; G06T 7/38; G06T 7/97; G06K 9/46; G06K 9/4604; A61B 6/5217
See application file for complete search history.

(56) References Cited

U.S. PATENT DOCUMENTS

| | | | | |
|---|---|---|---|---|
| 2003/0099390 | A1* | 5/2003 | Zeng et al. | 382/131 |
| 2009/0324031 | A1* | 12/2009 | Gee et al. | 382/128 |
| 2013/0004039 | A1* | 1/2013 | Masumoto | 382/128 |

OTHER PUBLICATIONS

Mattias P. Heinrich, et al., "Globally Optimal Deformable Registration on a Minimum Spanning Tree using Dense Displacement Sampling", Med Image Com put Com put Assist Interv, (2012), 15(Pt 3):115-22, 8 pages.

(Continued)

*Primary Examiner* — Andrew W Johns
(74) *Attorney, Agent, or Firm* — Oblon, McClelland, Maier & Neustadt, L.L.P.

(57) ABSTRACT

A medical imaging data processing apparatus for identifying an interface between anatomical features comprises a receiving unit configured to receive first medical imaging data that represents a region of a subject at a first time, and second medical imaging data that represents the region of the subject at a second, later time, a registration unit configured to perform a registration procedure to obtain registration data representative of a registration between the first medical imaging data and the second medical imaging data, and an interface identification unit configured to determine a variation of the registration data with location and to identify an interface between an anatomical feature and at least one further anatomical feature based on said variation of the registration data with location.

22 Claims, 6 Drawing Sheets

(56) References Cited

OTHER PUBLICATIONS

Yuri Boykov, et al., "An Experimental Comparison of Min-Cut/Max-Flow Algorithms for Energy Minimization in Vision", In IEEE Transactions on PAMI, vol. 26, No. 9, (Sep. 2004), pp. 1124-1137.
Bianca Lassen, et al., "Lung and Lung Lobe Segmentation Methods at Fraunhofer MEVIS", Proceedings of the Fourth International Workshop on Pulmonary Image Analysis, (2011), 185-199.

* cited by examiner

INTERFACE IDENTIFICATION APPARATUS AND METHOD

FIELD

The present invention relates to the identification of interfaces between anatomical features, for example the automatic identification of interfaces between anatomical features represented in medical imaging data.

BACKGROUND

A variety of medical imaging modalities, for example computerized tomography (CT), magnetic resonance imaging (MRI), positron emission tomography (PET) and ultrasound, have become standard techniques in obtaining medical imaging data representative of a patient or other subject for diagnostic or other purposes. Medical imaging data can be in a variety of forms and can include any suitable data obtained from measurements by a medical imaging modality and/or any suitable data representative of one or more anatomical features. Medical imaging data may comprise any data that can be rendered, or otherwise processed, to obtain an image of at least part of a patient or other medical subject and/or any data that can be rendered, or otherwise processed, to obtain an image of one or more anatomical features. Volumetric medical imaging data may, for example, be in the form of an array of voxels. Such arrays of voxels may for example be representative of intensity, absorption or other parameter as a function of three-dimensional position, and may for example be obtained by suitable processing of measurement signals obtained by a medical imaging modality.

A wide variety of image data processing techniques have been developed to support known imaging modalities. For example, a variety of techniques have been developed to segment automatically or semi-automatically medical imaging data obtained using such modalities to identify regions of the data that represent different anatomical or other features.

Many such known segmentation techniques are based on intensity values of voxels in the imaging data sets. For example, in the case of CT techniques, a CT data set usually comprises a three-dimensional array of voxels each representing a respective position in a three dimensional volume that includes the patient or other subject. Each voxel usually has an intensity value (for example in Hounsfield units) that represents the attenuation of X-rays at the corresponding position in the volume, as determined from the CT measurements. In a simple case, a segmentation can be performed based solely on a thresholding of the voxel intensity values. For example, all voxels having intensity values in a particular range may be considered to represent bone.

Many more complex segmentation procedures have been developed based on intensity values, in which for example one or more of pattern recognition, fitting processes, morphological processes, comparison to atlases or other references, or other processes can be used to segment the medical imaging data.

It is also known to obtain multiple medical imaging data sets on the same patient or other subject by performing measurements at different times, under different conditions or using different modalities. Such multiple medical imaging data sets often have different co-ordinate systems such that the same anatomical feature of the subject will appear at positions having different co-ordinates in the different medical imaging data sets (for example, in a simple case, due to the patient or other subject having a different relative position within the scanner when the different imaging data sets were obtained).

It is known to register different medical imaging data sets, for example different medical imaging data sets for the same patient or other subject obtained at different times, to obtain registration data that comprises or represents a transformation of co-ordinates for one or both of the medical imaging data sets. By transforming the co-ordinates of one or both medical imaging data sets it can be provided that the medical imaging data sets are aligned such that the same anatomical features from the medical imaging data sets appear at substantially the same, or corresponding, positions in a common co-ordinate system.

It is known to perform registrations manually or automatically using known analysis techniques. Different types of registration may be used, for example rigid, affine, or non-rigid.

A rigid registration in this context may comprise a registration in which the co-ordinates of data points in one data set are subject to rotation and translation in order to register the data set to another data set. An affine registration in this context may comprise a registration in which the coordinates of data points in one dataset are subject to rotation, translation, scaling and/or shearing in order to register the dataset to another dataset. Thus, a rigid registration may be considered to be a particular type of affine registration.

Non-rigid registrations can provide different displacements for each voxel of the data set to be registered and can, for example, use non-linear transformations, in which the coordinates of data points in one dataset are subject to flexible deformations in order to register the data set to another data set. Non-linear transformations may in some cases be defined using vector fields such as warp fields, or other fields or functions, defining an individual displacement for each voxel in a three-dimensional data set.

It is known to use multiple registered medical imaging data sets in performing segmentation procedures. For example, in segmenting or imaging the vasculature it is known to introduce contrast agent into blood vessels of a patient, to obtain CT data of the patient when no contrast agent is present in a region of interest, and to obtain further CT data when the contrast agent is present in the region of interest. By registering the data sets, and subtracting or performing other processes on the registered data sets, the blood vessels can be displayed or identified based on the variation of intensities between the data sets due to the presence of contrast agent.

The accurate segmentation of some anatomical features in medical image data sets can be difficult, for example if they are close to other similar anatomical features or if they have intensity values that are close to intensity values of other anatomical features. Features that are small or have complex shapes can also sometimes be difficult to segment accurately.

It is known to perform CT imaging measurements of the lungs of a patient or other subject. Automatic analysis and effective visualization of the lungs can be dependent on the quality of segmentation and classification of the lungs. Segmentation of lung features, for example pulmonary fissures that separate the different lung lobes, can be difficult as in CT scans the pulmonary fissures can be indistinct and hard to track. Similarly, in some cases it can be challenging to distinguish between a chest wall and lung due to their close proximity.

BRIEF DESCRIPTION OF THE DRAWINGS

Embodiments are now described, by way of non-limiting example, and are illustrated in the following figures, in which.

DETAILED DESCRIPTION

Certain embodiments provide a medical imaging data processing apparatus for identifying an interface between anatomical features comprising a receiving unit configured to receive first medical imaging data that represents a region of a subject at a first time, and second medical imaging data that represents the region of the subject at a second, later time, a registration unit configured to perform a registration procedure to obtain registration data representative of a registration between the first medical imaging data and the second medical imaging data, and an interface identification unit configured to determine a variation of the registration data with location and to identify an interface between an anatomical feature and at least one further anatomical feature based on said variation of the registration data with location.

Certain embodiments provide a method of identifying an interface between anatomical features comprising receiving first medical imaging data that represents a region of a subject at a first time, and second medical imaging data that represents the region of the subject at a second, later time, performing a registration procedure to obtain registration data representative of a registration between the first medical imaging data and the second medical imaging data, determining a variation of the registration data with location, and identifying an interface between an anatomical feature and at least one further anatomical feature based on said variation of the registration data with location.

Certain embodiments provide a scanner system comprising a scanner configured to perform measurements on a subject to obtain first medical imaging data that represents a region of the subject at a first time, and second medical imaging data that represents the region of the subject at a second, later time, a registration unit configured to perform a registration procedure to obtain registration data representative of a registration between the first medical imaging data and the second medical imaging data, and an interface identification unit configured to determine a variation of the registration data with location and to identify an interface between an anatomical feature and at least one further anatomical feature based on said variation of the registration data with location.

Figure 1:
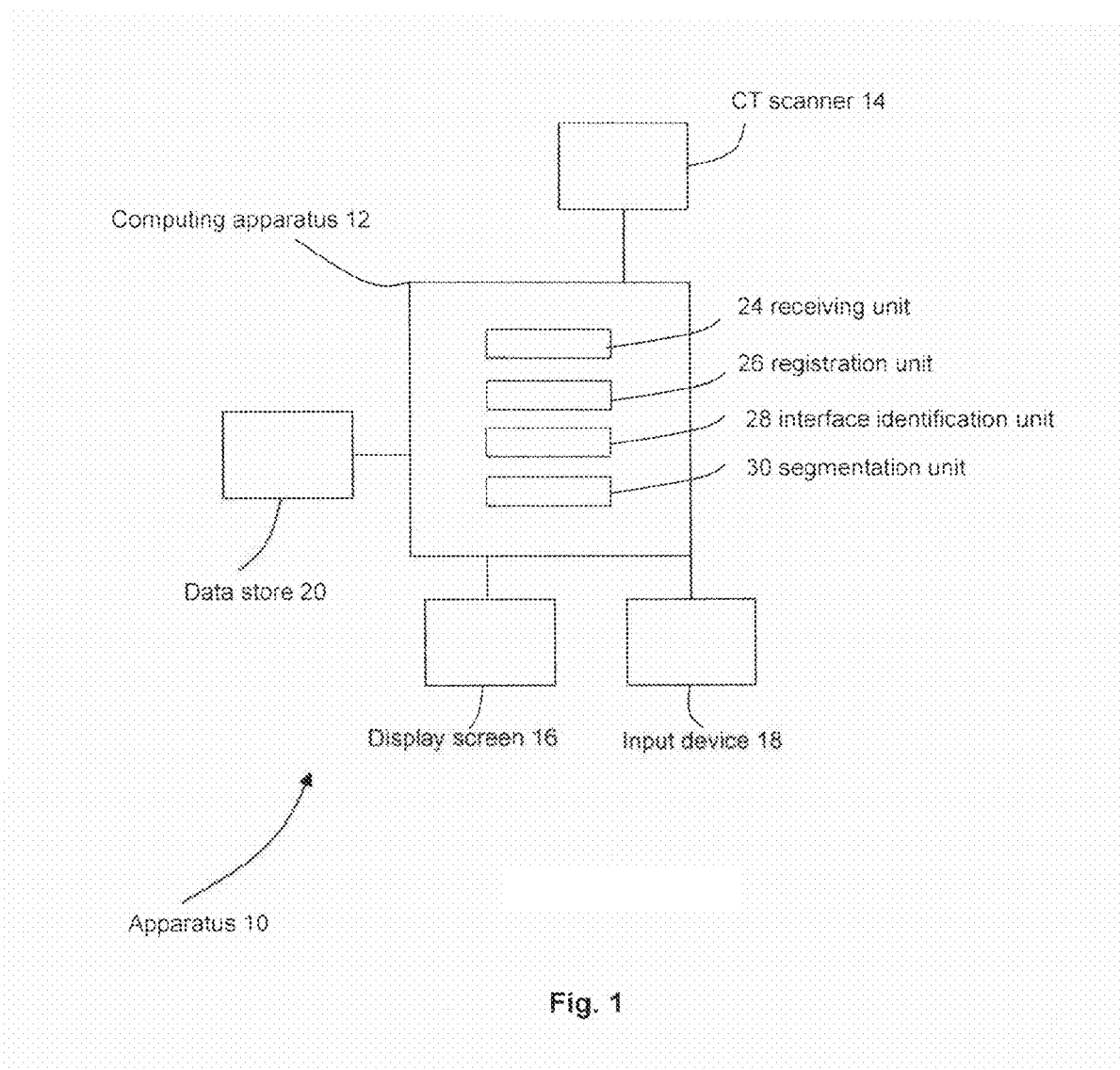
FIG. 1 is a schematic illustration of an imaging data processing apparatus and associated scanner, forming a scanner system, according to an embodiment.

An imaging data processing apparatus 10 according to an embodiment is illustrated schematically in FIG. 1.

The imaging data processing apparatus 10 comprises a computing apparatus 12, in this case a personal computer (PC) or workstation, that is connected to a CT scanner 14, a display screen 16 and an input device or devices 18, such as a computer keyboard and mouse. In the present embodiment, imaging data is obtained by the CT scanner 14 and stored in data store 20. In other embodiments, imaging data may be loaded from a remote data store or other memory. Any suitable CT scanner may be used.

Computing apparatus 12 provides a processing resource for receiving and processing medical imaging data. Computing apparatus 12 includes a receiving unit 24 for receiving medical imaging data from the CT scanner 14, from the data store 20 or from a remote data store or other memory. Computing apparatus 12 also includes a registration unit 26 for performing a registration process to register sets of medical imaging data, an interface identification unit 28 configured to identify interfaces between anatomical or other regions based on registration data, and a segmentation unit 30 for performing further segmentation processes to segment various anatomical or other regions.

In the present embodiment, the receiving unit 24, the registration unit 26, the interface identification unit 28 and the segmentation unit 30 are each implemented in computing apparatus 12 by means of a computer program having computer-readable instructions that are executable by a central processing unit (CPU) of the computing apparatus to perform the method of the embodiment. However, in other embodiments, the various units may be implemented as one or more ASICs (application specific integrated circuits) or FPGAs (field programmable gate arrays) or other dedicated circuitry.

The computing apparatus 12 also includes a hard drive and other components of a PC including RAM, ROM, a data bus, an operating system including various device drivers, and hardware devices including a graphics card. Such components are not shown in FIG. 1 for clarity.

It is a feature of the embodiment of FIG. 1 that it is configured to perform a process to identify interfaces between anatomical or other regions based on registration of medical imaging data and a variation with location of registration data obtained from or representing such registration. A process according to an embodiment is illustrated in overview in the flow chart of FIG. 2.

At stage 40, the receiving unit 24 receives a first set of medical imaging data and a second set of imaging data, which were obtained from scans performed by the CT scanner 14 on the same region of a subject but at different times. In this case, the first set of medical imaging data is CT scan data representative of the chest cavity region of a patient and including CT data representing the patient's lungs in an inhalation state (for example, when the patient was in the process of exhaling or had substantially fully inhaled), and the second set of medical imaging data is CT scan data representative of the chest cavity region of the patient and including CT data representing the patient's lungs during a subsequent exhalation state (for example, when the patient was in the process of exhaling or had substantially fully exhaled).

Both sets of CT scan data in this case comprise volumetric data comprising a three-dimensional array of voxels, each voxel having a position value representative of the position the voxel corresponds to in the scanned volume, and an intensity value representative of attenuation of X-ray radiation of the CT scan at that position.

At stage 40, the registration unit 26 registers the first set of imaging data with the second set of imaging data using a non-rigid registration procedure. Any suitable non-rigid registration procedure may be used. A deformation field is obtained from the non-rigid registration. In the present embodiment, the deformation field is a dense vector field, in which an individual displacement vector is defined for each voxel. In the present embodiment, a discrete optimization with dense displacement sampling (DEEDS) algorithm is used. See, for example, Heinrich et al, Globally optimal deformable registration on a minimum spanning tree using dense displacement sampling, Med Image Comput Comput Assist Interv, 2012; 15(Pt 3):115-22. Any other suitable registration procedure may be used in alternative embodiments. For example any suitable registration algorithm, such as a non-rigid registration algorithm, that is able to distinguish differential motion at different locations within the medical imaging data sets may be used.

The output of the registration procedure performed by the registration unit 26 at stage 40 is a set of registration data that represents an offset in co-ordinates for a plurality of locations in the second imaging data set that align those locations with corresponding locations in the first imaging data set. Thus, for example, if the registration were perfect and if the co-ordinates of each voxel in the second imaging data set were to be transformed in accordance with the registration data then corresponding anatomical features (for example lung features or other organ features) would be represented at substantially the same positions in the first imaging data set and in the transformed second imaging data set.

In the present embodiment, the registration data comprise a warp field that comprises, for each voxel of the second imaging data set, a respective vector that comprises a direction and magnitude of displacement of that voxel required to align it with a corresponding voxel of the first imaging data set. Any suitable type of registration data may be used in other embodiments, for example any suitable vector field or any other suitable field or function, or any other suitable data that represents a registration or transformation between co-ordinates.

Figure 3:
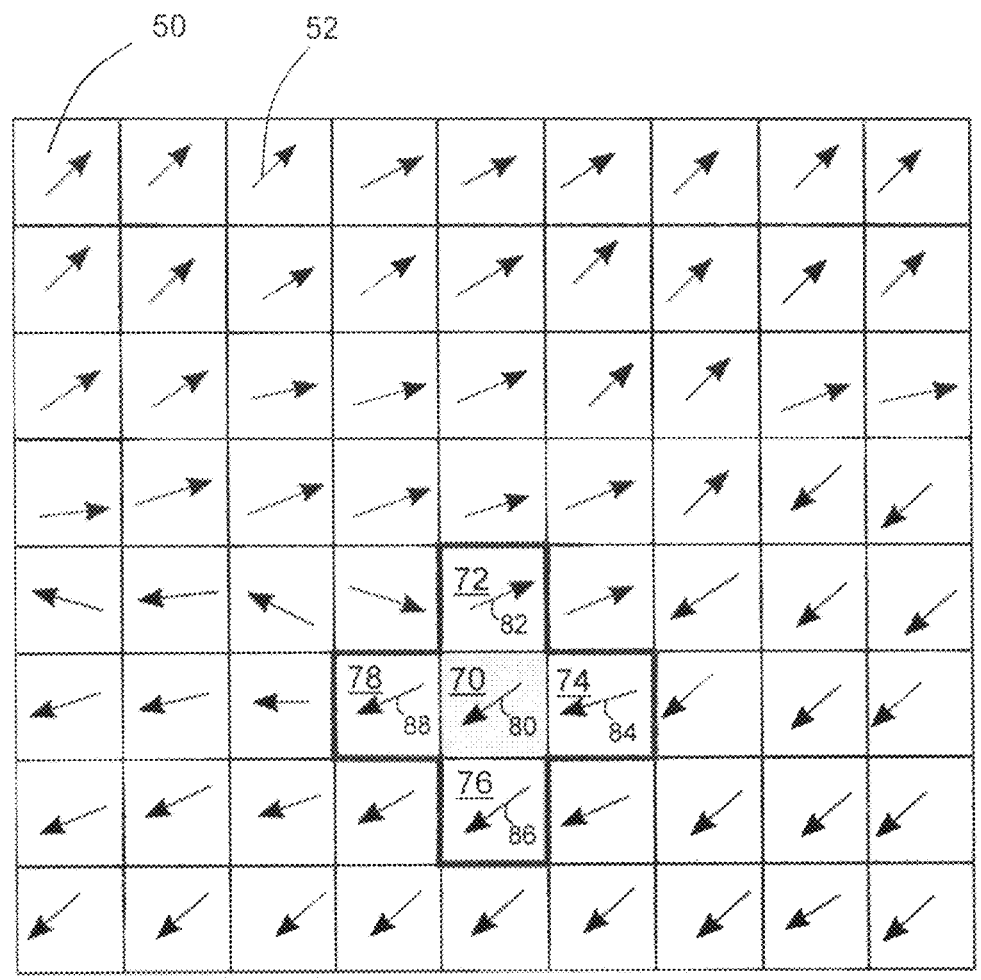
FIG. 3 is a schematic illustration showing representations of warp field vectors or registration data for an array of voxels.

The vectors of the warp field for a plurality of voxels 50 of a region of the second imaging data set are illustrated schematically by arrows 52 in FIG. 3. The arrows 52 represent the direction of the vectors; the magnitude of the vectors is not represented in FIG. 3. It can be seen that for a part of the region all of the arrows 52 point left to right and for another part of the region the arrows point right to left. The different directions of the vectors suggest that different parts of the patient's anatomy have moved relative to each other between the first scan and the second scan. In this case, the different parts of the patient's anatomy that have moved relative to each other are different lobes of a lung of the patient, whose surfaces have slid relative to each other when the patient exhaled, between the first scan and second scan. The voxels of FIG. 3 represent a small part of a region at a boundary region between the lung lobes.

Figure 4A:
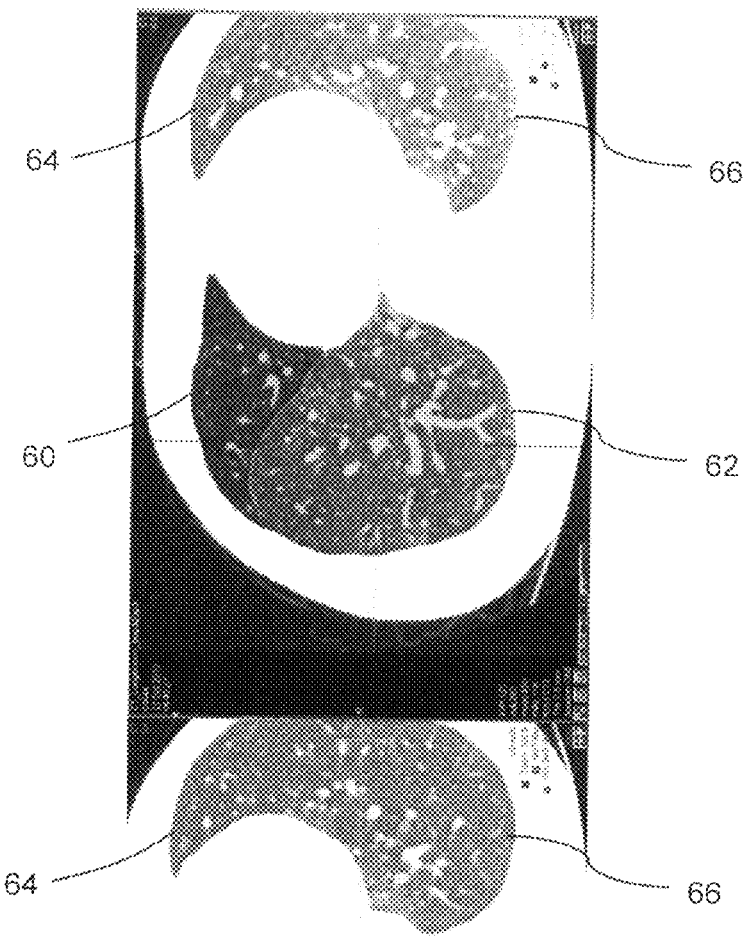
FIGS. 4a and 4b show scan images of lung lobes during exhalation and inhalation phases.
Figure 4B:
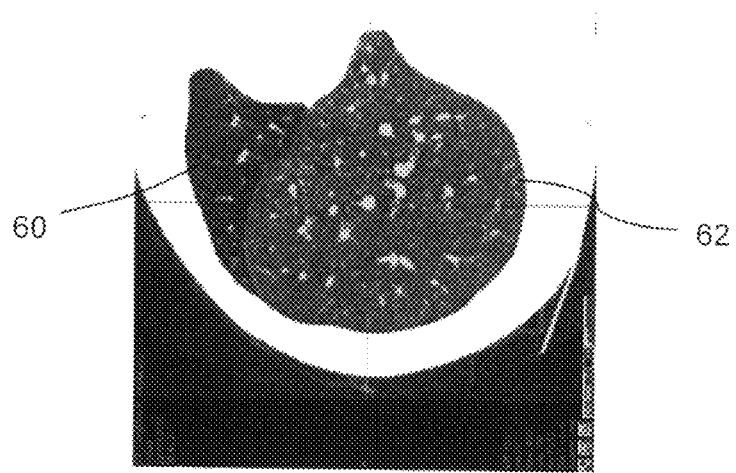

The lung lobes 60, 62 of a first of the patient's lungs and the lung lobes 64, 66 of the second of the patient's lungs are shown in FIGS. 4a and 4b. FIG. 4a is a rendered image representative of a slice through the patient's lungs obtained by processing the first medical imaging data set (acquired towards the end of an exhalation phase) using suitable known image data processing techniques (in this case, an MPR slice image), and FIG. 4b is a rendered image representative of a slice through the patient's lungs obtained from the first medical imaging data set (acquired towards the end of an inhalation phase). The lung lobes have increased in size during inhalation. The lung lobes 60, 62 have slid relative to each other during inhalation, and the lung lobes 64, 66 have also slid relative to each other during inhalation. The embodiment of FIG. 2 exploits the fact that the surfaces of the lobes can move at least partly independently of each other under respiration. The surface of the lobes are generally not anatomically connected to each other at the points where they contact each other and can slide against each other and against the chest wall.

Figure 2:
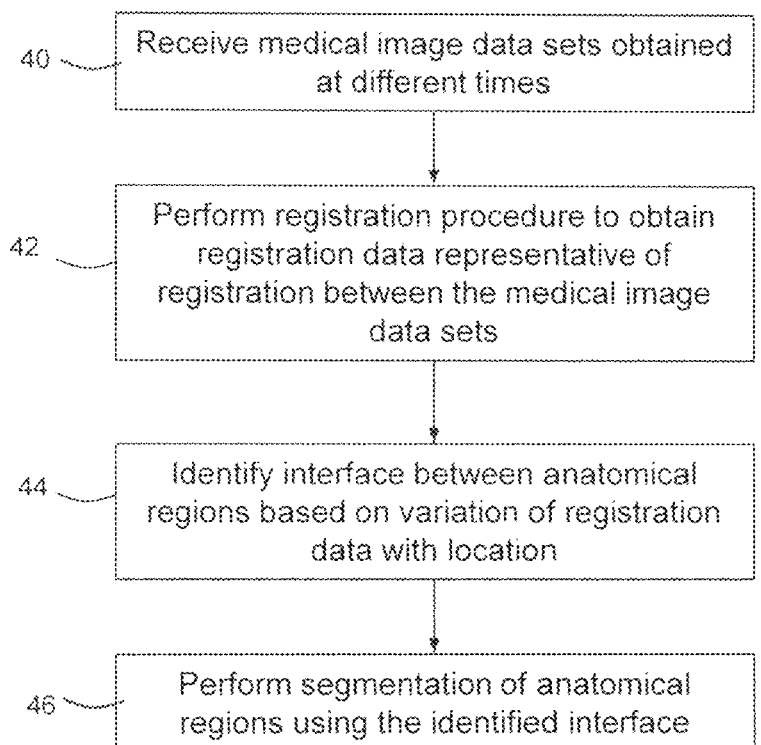
FIG. 2 is a flow chart illustrating in overview an imaging data processing method according to an embodiment.

It is a feature of the embodiment of FIG. 2 that the relative movement of different anatomical features between scans can be used to identify an interface between such features, by suitable processing of the registration data. Such a processing of the registration data occurs in the present embodiment at stage 44 of the process of FIG. 2, at which a variation of the registration data with location is determined and used to identify a boundary between anatomical regions.

In the embodiment of FIG. 2, for each voxel location in the registered second imaging data set, the registration data for that location (e.g. the vector of the warp field for that location) is used in a process that enables variation of the registration data with location to be determined.

Considering one voxel location 70 in particular by way of example, the process in this case comprises determining the dot product of the vector 80 of the warpfield for that location 70 and the vector 82, 84, 86, 88 for each of the closest surrounding voxel locations 72, 74, 76, 78. The value of the dot product depends on the cosine of the angle between the pair of vectors (80 and 82, 84, 86 or 88) as well as the magnitude of the vectors. The value of cosine of the angle between the pair of vectors varies from a value of +1 (if the vectors are aligned in the same direction, e.g. parallel) to a value of −1 (if the vectors are aligned but in opposite directions, e.g. anti-parallel).

The results of the dot product determinations (four in this example) are then used as a measure of the difference in vector direction for the voxel location 70 compared to the surrounding locations. It can be seen in this case that the dot product between the vectors 80, 82 (of voxel locations 70, 72) will have a relatively large negative value as the vectors 80, 82 are aligned in substantially antiparallel directions, whereas the dot products between the vectors 80 of voxel location 70) and 84, 86 or 88 (of voxel locations 74, 76, 78) will have a relatively large positive value as the vectors 80, 84, 86, 88 are aligned in substantially the same direction.

Although in the example of FIG. 3, dot products are described calculated for each of the four nearest voxels in two dimensions, it will be understood that the data can be three-dimensional data there may be six nearest neighbor voxels for which dot products are calculated. In alternative embodiments, dot products or any other suitable measures of difference between registration data, can be calculated in respect of more of the surrounding voxels, not only the nearest neighbor voxels.

The measure of difference in the registration data, such as vector direction and/or magnitude, for example as provided by the dot products, can be referred to as discontinuity data as it represents, or can be used to identify, where the registration data changes significantly. The difference in vector direction and/or magnitude between voxels may be taken as representative of a level of discontinuity between the voxels that is present. Any suitable discontinuity data may be used in alternative embodiments, for example any data that is representative of variation of one or more properties of the registration and that can be used to determine change or rate of change of such variation as a function of location. The discontinuity data may represent a level of discontinuity that is present according to any suitable measure.

At stage 44 of the process of the embodiment of FIG. 2 the calculation of dot products between a vector at a location and vectors at surrounding locations is repeated for each of the voxel locations. The values of the dot products are then compared to a threshold, and those pairs of voxel locations that provide a dot product value that is negative and of greater magnitude than the threshold value are identified as voxels that are potentially separated by an interface between anatomical regions. Thus, in the example discussed above in relation to voxel position 70, the interface between voxels 70, 72 may be identified as representing a possible interface between anatomical regions as it has a relatively large negative value.

Figure 5:
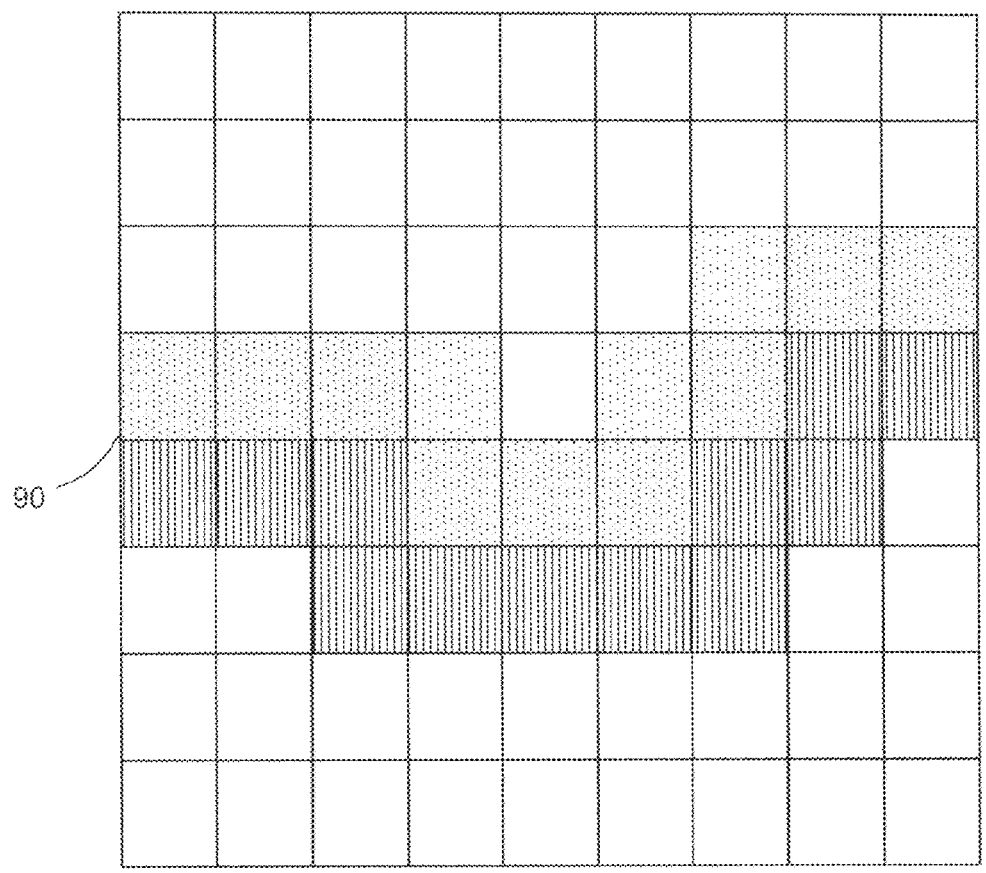
FIG. 5 is a schematic illustration of the array of voxels of FIG. 3 and indicating voxels that have been classified as being on either side of a boundary between anatomical regions.

The threshold comparison is repeated for all of the calculated dot products and all of the voxel positions, and all of the voxel interfaces that potentially represent, or are associated with, an interface between anatomical features are identified based on the comparison. FIG. 5 identifies those voxel pairs that are identified as being separated by a voxel interface that potentially represents an interface between anatomical structures, with voxels of the pairs on one side of the interface being filled with dots, and voxels of the pairs on the other side of the interface being filled with vertical lines. In this case, it can be seen that the interfaces between voxels of the identified voxel pairs form a single, continuous line 90, and that line is taken as representing an interface between anatomical features (in this case, different lung lobes).

In practice, depending on the threshold value that is used and the registration data, there may be gaps between pairs of voxels that are identified as representing a possible interface between anatomical features, such that the identified voxel interfaces together do not form a single continuous interface. In that case, any suitable process can be used to join the individual voxel interfaces to form a single interface between anatomical features. For example, the separated, non-continuous voxel interfaces can be joined by the shortest path between them to form the interface between anatomical features. Alternatively, for example, the separated, non-continuous voxel interfaces can be joined by a path between the most discontinuous voxel pairs (e.g. having the highest negative dot product values, even if those values do not exceed the threshold) that are present between the separated, non-continuous voxel interfaces.

In other cases, the thresholding process may identify interfaces between pairs of voxels that form alternative paths, such that a single continuous interface between anatomical features cannot immediately be identified. In that case the interface identification unit 28 can perform a further selection process to select a single one of the paths that seems to be most likely to represent an interface between anatomical features. For example, the path that seems to provide the greatest discontinuity between registration data (for example, the greatest negative dot product values) may be selected.

In some embodiments, the thresholding process may be repeated by the interface identification unit 28 for different values of the threshold until the voxel interfaces that are identified form a single, substantially continuous line, which can then be taken as representing the interface between anatomical features.

In alternative embodiments, any suitable alternative process can be used to identify an interface between anatomical features based on variation of registration data with location, and the process is not restricted to using a thresholding or to using dot products. For example any suitable fitting, clustering or other process can be used to identify a path through the region represented by the imaging data for which differences between registration data (for example magnitude and/or vector direction) on either side of the path are maximized. The path can then be taken as representing an interface between anatomical features.

The interface between anatomical features identified at stage 44 of the process of FIG. 3 can be used for a variety of purposes. For example, a line or other graphical feature representing the interface can be overlaid or otherwise displayed on images obtained from the medical imaging data sets, for example 2D or 3D rendered images. Alternatively, the interface can be used in a selection of data from one or both of the imaging data sets (for example selection of data on one or other side of the interface) for use in any desired subsequent process.

Figure 6:
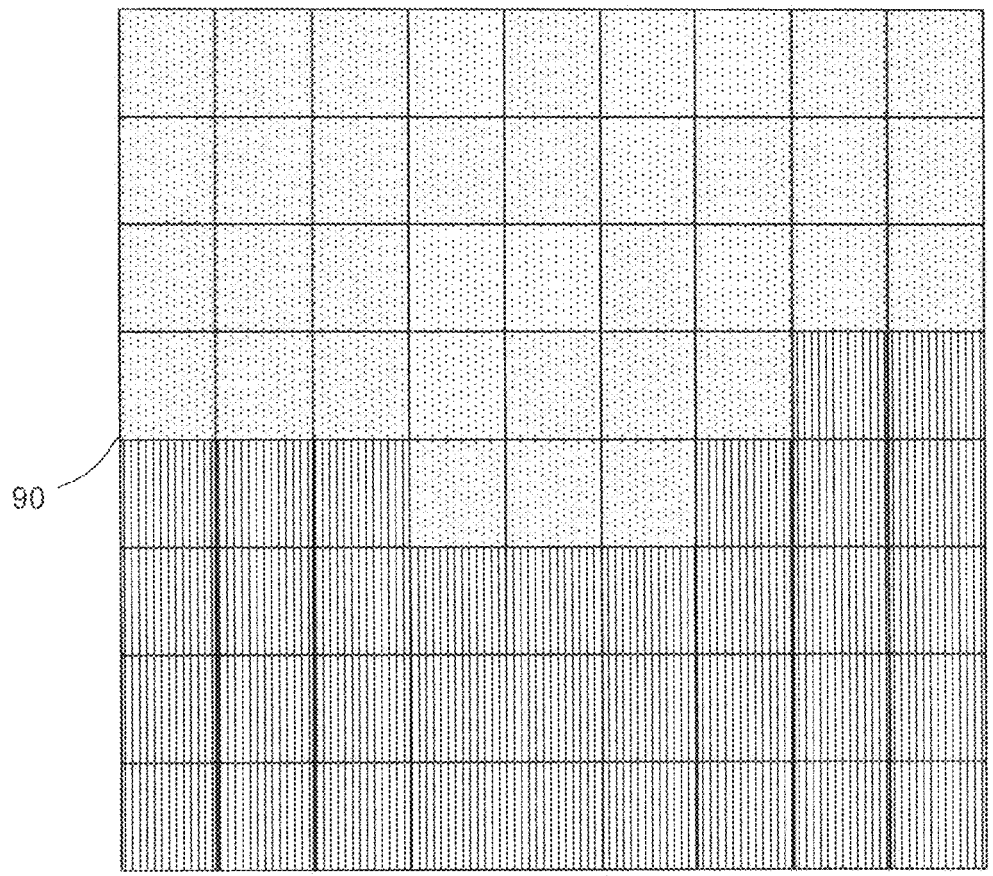
FIG. 6 is a schematic illustration of the array of voxels of FIG. 5 after a flood algorithm has been applied to classify voxels on either side of the boundary.

In the embodiment of FIG. 2, the identified interface between anatomical features is used at stage 46 in a subsequent segmentation process. In this case, a flood fill algorithm is used to classify the interiors of regions separated or bounded at least in part by the identified interface as belonging to one or other of the anatomical features separated by the interface (for example, one or other of the lung lobes). The flood fill algorithm may be, for example, a Graph Cut Minimum-cut Maximum-flow algorithm as described in, for example, Y Boykov and V Kolmogorov, An Experimental Comparison of Min-Cut/Max-Flow Algorithms for Energy Minimization in Vision, In IEEE Transactions on PAMI, Vol. 26, No. 9, pp. 1124-1137, September 2004. The results of such a flood-fill based segmentation algorithm applied to the data of FIG. 5 are illustrated schematically in FIG. 6. In FIG. 6 all of the voxels on one side of the interface identified at stage 42 have been classified as belonging to one of the lung lobes (as indicated by filling with dots) and all of the voxels on the other side of the interface have been classified as belonging to the other of the lung lobes (as indicated by filling with vertical lines).

In practice, any suitable segmentation algorithm can be used, with the identified interface between anatomical features being used as one of the inputs to the segmentation algorithm. If a flood fill-based segmentation algorithm is used then it may be an algorithm that is configured to deal with the interfaces potentially not being closed, depending on the imaging data and the anatomical features that are the subject of the data. For example, in the case of the lung lobes, the lobes are connected at the main bronchial branches and so even if the interfaces around the lobes are mapped in their entirety they will not be completely closed. The segmentation algorithm may include additional processes in accordance with any suitable known techniques, for example pattern matching, clustering, machine learning, thresholding and other processes including morphological processes such as opening, closing or fill operations, that can be used to supplement the segmentation based on the identified interface. Such additional processes can be used to segment the anatomical features in the imaging data whether or not the interface or interfaces are open or closed.

The embodiment of FIG. 2 is able to automatically classify the different lobes of a lung or lungs. A correct classification can be used in various clinical application protocols including analysis and visualization. A classification of the lung lobes can also be used to accurately separate the lung lobes from the chest walls.

In the particular example described above in relation to the embodiment of FIG. 2, the apparatus is used to process medical imaging data to identify an interface between different lung lobes. Embodiments can however be used to identify an interface or interfaces between any suitable anatomical features, for example between at least part of a lung and at least part of a chest wall, or between tendon, muscle, cartilage or bone (for example, between tendon and muscle or between one muscle and another muscle etc.). Embodiments can be particularly well suited for identifying interfaces between anatomical features that move relative to each other in normal operation of the human or animal body, even if the features are closely spaced or difficult to distinguish using known techniques.

The registration data in the particular example described above in relation to the embodiment of FIG. 2 comprises warp field data. In alternative embodiments the registration data may comprise any suitable type of data, for example any suitable type of vector or vector field data. The registration data does not necessarily comprise separate registration data entries for each voxel in some embodiments, and may represent a registration between the data sets in the co-ordinate space of the voxels without necessarily including data entries specifically associated with particular voxels. For example, the registration data may comprise a parametric representation of a vector field, and the interface identification unit may identify interfaces based on values of a spatially varying gradient, or higher order derivative, of the vector field. For example, if the spatially varying gradient, or higher order derivative of the vector field indicates that there is a region where the registration data changes sufficiently rapidly, for example substantially discontinuously, the interface identification unit may identify that region as an interface region.

Embodiments have been described in relation to the processing of medical imaging data sets comprising CT data. Any suitable data sets may be used in alternative embodiments, for example magnetic resonance imaging (MRI) data sets, positron emission tomography (PET) data sets, or ultrasound data sets.

Although embodiments have been described in relation to an example in which an interface is identified based on variation of registration data for a registration between two medical imaging data sets, any suitable medical imaging data for example any suitable number of medical imaging data sets can be used in alternative embodiments. For example, multiple registrations can be performed to obtain multiple sets of registration data or a combined set of registration data, and variation(s) within and/or between the multiple sets of registration data or the combined set of registration data can be used to determine the interface.

In some cases the interface may comprise a boundary region of multiple voxel thickness comprising further material, for example further anatomical material, between the anatomical region and further anatomical region. In embodiments, the boundary region may be identified and/or classified based on the variation of registration data with location. In some embodiment, a first interface may be identified between the anatomical feature and the further material based on the variation of registration data with location, and a second interface may be identified between the further material and the further anatomical region based on the variation of registration data with location.

Certain embodiments provide for the registration of two or more scans that are at different phases of a respiration cycle, and the analysis of a warp motion field to find areas with discontinuities. Areas with high discontinuities can be taken as corresponding to interfaces between lung lobes. A segmentation mask volume is calculated by filling in regions bounded by the discontinuities.

Certain embodiments provide a method for segmenting and classifying objects from within a set of medical image scans, wherein each scan occurs at different time points, a registration algorithm determine a change in position of points within the scans, discontinuities in the derived registration data are used to determine the location of at least one interface between objects within the scan, and the at least one interface between objects is used to classify a location of at least one of the objects. The lobes of the lung may be segmented automatically based on an inspiration/expiration study. A segmentation may be performed using a hybrid of motion registration discontinuity analysis and existing object segmentation techniques. Alternatively or additionally, other anatomical structures may be segmented automatically.

Many known classification and segmentation techniques are based only on the data values in a single scan or subtracted data values in a pair of scans. In contrast, in certain embodiments, by using motion information objects can be classified that do not necessarily have large intensity gradients between them. Embodiments can be useful in a variety of contexts, for example in relation to 4D orthopaedic scans where movement is captured, or in augmenting or replacing existing single phase lung segmentation techniques.

It will be well understood by persons of ordinary skill of the art that embodiments may implement certain functionality by means of a computer program or computer programs having computer-readable instructions that are executable to perform the method of the embodiments. The computer program functionality could be implemented in hardware (for example by means of CPU). The embodiments may also be implemented by one or more ASICs (application specific integrated circuit) or by a mix of hardware or software.

Whilst particular units have been described herein, in alternative embodiments functionality of one or more of these units can be provided by a single unit, or functionality provided by a single unit can be provided by two or more units in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging data processing apparatus for identifying an interface between anatomical features comprising:
   processing circuitry:
      configured to receive first medical imaging data that represents a region of a subject at a first time, and second medical imaging data that represents the region of the subject at a second, later time;
      configured to perform a registration procedure to obtain registration data representative of a registration between the first medical imaging data and the second medical imaging data; and
      configured to determine a variation of the registration data with location and to identify an interface between an anatomical feature and at least one further anatomical feature based on said variation of the registration data with location.

2. Apparatus according to claim 1, wherein the anatomical feature comprises at least part of a lung lobe and the at least one further feature comprises at least part of a further lung lobe.

3. Apparatus according to claim 1, wherein the anatomical feature comprises at least part of a lung and the at least one further anatomical feature comprises at least part of a chest wall.

4. Apparatus according to claim 1, wherein the anatomical feature comprises tendon, muscle, cartilage or bone and the further anatomical feature comprises tendon, muscle, cartilage or bone.

5. Apparatus according to claim 1, wherein the first medical imaging data represents the region of a subject in one of an inhalation state or exhalation state and the second medical imaging data represents the region of the subject in the other of an inhalation state or exhalation state.

6. Apparatus according to claim 1, wherein said variation of registration data with location is representative of movement of said anatomical feature relative to said further anatomical feature.

7. Apparatus according to claim 6, wherein said movement comprises a sliding of said anatomical feature relative to said further anatomical feature at said interface between said anatomical feature and said further anatomical feature.

8. Apparatus according to claim 1, wherein the determining of a variation of the registration data with location comprises obtaining discontinuity data representative of a level of discontinuity in the registration data as a function of location.

9. Apparatus according to claim 8, wherein the interface identification is configured to compare the discontinuity data to a threshold and to identify the interface between anatomical regions in dependence on the comparison.

10. Apparatus according to claim 1, wherein the interface identification is configured to identify a discontinuity in the registration data and to identify the interface based on the identified discontinuity.

11. Apparatus according to claim 1, wherein the registration data comprises vector data, and the determining of variation of registration data with location comprises determining a difference in vector direction for registration data at at least two different locations.

12. Apparatus according to claim 1, wherein the registration data comprises vector data, and the determining of variation of registration data with location comprises determining, for each of a plurality of locations, a dot product between vector data for the location and vector data for at least one further location.

13. Apparatus according to claim 1, wherein the registration data is representative of, for each a plurality of locations within the region, an offset of co-ordinates between the first medical imaging data and the second medical imaging data determined according to the registration procedure.

14. Apparatus according to claim 1, wherein the registration procedure comprises a non-rigid registration procedure.

15. Apparatus according to claim 1, wherein the registration data comprises at least one of vector field data or warpfield data.

16. Apparatus according to claim 1, the processing circuitry further configured to use the identified interface in a segmentation procedure for segmenting the anatomical feature and at least one further anatomical feature.

17. Apparatus according to claim 16, wherein the segmentation procedure comprises performing a fill process to at least partly fill at least one region that is at least partly bounded by the identified interface.

18. Apparatus according to claim 1, wherein the medical imaging data comprises at least one of computerized tomography (CT) data, magnetic resonance imaging (MRI) data, positron emission tomography (PET) data, or ultrasound data.

19. Apparatus according to claim 1, wherein the first medical imaging data and the second medical imaging data each comprises a respective three dimensional array of voxels.

20. A method of identifying an interface between anatomical features comprising:
    receiving first medical imaging data that represents a region of a subject at a first time, and second medical imaging data that represents the region of the subject at a second, later time;
    performing a registration procedure to obtain registration data representative of a registration between the first medical imaging data and the second medical imaging data;
    determining a variation of the registration data with location; and
    identifying an interface between an anatomical feature and at least one further anatomical feature based on said variation of the registration data with location.

21. A non-transitory computer-readable storage medium storing instructions that are executable to perform a method according to claim 20.

22. A scanner system comprising:
    scanner circuitry configured to perform measurements on a subject to obtain first medical imaging data that represents a region of the subject at a first time, and second medical imaging data that represents the region of the subject at a second, later time;
    processing circuitry:
       configured to perform a registration procedure to obtain registration data representative of a registration between the first medical imaging data and the second medical imaging data; and
       configured to determine a variation of the registration data with location and to identify an interface between an anatomical feature and at least one further anatomical feature based on said variation of the registration data with location.

* * * * *